United States Patent [19]

Müller et al.

[11] Patent Number: 4,599,405

[45] Date of Patent: Jul. 8, 1986

[54] PROCESS FOR THE PRODUCTION OF IRON(III)HYDROXIDE/DEXTRAN COMPLEXES AND A STERILE PHARMACEUTICAL SOLUTION CONTAINING THEM

[75] Inventors: Arthur Müller, St. Gall; Walter Richle, Lustmühle, both of Switzerland

[73] Assignee: Laboratorien Hausmann AG, St. Gall, Switzerland

[21] Appl. No.: 687,152

[22] Filed: Dec. 28, 1984

Related U.S. Application Data

[63] Continuation of Ser. No. 283,146, Jul. 14, 1981, abandoned.

[30] Foreign Application Priority Data

Jul. 16, 1980 [DE] Fed. Rep. of Germany ....... 3026868

[51] Int. Cl.$^4$ ............................................. C08B 37/02
[52] U.S. Cl. .................................................... 536/113
[58] Field of Search ......................................... 536/113

[56] References Cited

U.S. PATENT DOCUMENTS 3,666,749  5/1972  Reumert et al. .................... 536/113

FOREIGN PATENT DOCUMENTS

| 1196629 | 3/1966 | Fed. Rep. of Germany . |
| 1954960 | 5/1970 | Fed. Rep. of Germany ...... 536/113 |
| 1768361 | 9/1971 | Fed. Rep. of Germany . |
| 2659799 | 7/1977 | Fed. Rep. of Germany . |
| 370194  | 6/1963 | Switzerland . |

*Primary Examiner*—Nicky Chan
*Attorney, Agent, or Firm*—Schwartz, Jeffery, Schwaab, Mack, Blumenthal & Evans

[57] ABSTRACT

A process for the production of iron(III)hydroxide/-dextran complexes in which from 2.0 to 2.6 vals of carbonate are slowly added to an acid solution containing a partially depolymerized dextran having an average molecular weight of from 1000 to 10,000 and an iron(III)salt, from 50 to 100 kg of iron ions being used per 100 kg of dextran, after which an alkali metal hydroxide or ammonium hydroxide is added to the solution in such a quantity that, including the carbonate added, approximately 3 vals of anions are added until a pH value of no less about 10.5 is reached, the suspension formed is converted into a solution by heating and the solution is worked up in known manner.

The invention also relates to sterile pharmaceutical solutions containing these complexes.

11 Claims, No Drawings

PROCESS FOR THE PRODUCTION OF IRON(III)HYDROXIDE/DEXTRAN COMPLEXES AND A STERILE PHARMACEUTICAL SOLUTION CONTAINING THEM

This is a continuation of application Ser. No. 283,146, filed July 14, 1981, now abandoned.

This invention relates to a process for the production of iron(III)hydroxide/dextran complexes in which an alkali carbonate, ammonium carbonate or a carbonate of an organic base that is inert to the reaction components is added to an acid solution containing a partially depolymerised dextran and an iron(III)salt, after which an alkali metal hydroxide or ammonium hydroxide is added, the suspension formed is converted into a solution by heating and the solution is worked up in known manner.

There are several known processes for the production of non-ionic, therapeutically useable iron(III)hydroxide/dextran complexes. The process outlined at the beginning is described for example in German Pat. No. 1,196,629 and gives excellent preparations which have been very successfully used for controlling iron deficiencies in humans and animals. However, the solutions of these complexes as used for injection purposes only contain up to about 10% by weight of iron (W/V). ("W" stands for "weight" whilst "V" stands for "volume"). There is a considerable need to provide iron/dextran complexes from which it is possible to obtain injectable solutions having a higher iron content.

U.S. Pat. Nos. 3,536,696 and 3,639,588 describe iron(III)hydroxide complexes containing dextran heptonic acid as complexing agent. Dextran heptonic acid is difficult to produce with the result that the process as a whole is not very satisfactory.

German Offenlegungsschrift No. 17 68 361 describes a process for the production of iron(III)hydroxide complexes in which an aqueous solution of an iron(III)salt is slowly neutralised with alkali, an aqueous solution of a dextran is then added, the pH-value of the solution is adjusted to between 4 and 7 and the solution is subsequently heated to form the complex. Injectable solutions containing up to 25% by weight of iron, based on the volume of the solution, are said to be able to be produced from complexes of this type. The disadvantage of this known process lies in the fact that only certain (oxidised) dextrans can be dissolved at pH 4 to 7, whereas pH-values higher than 7 are required for other dextrans (non-oxidised) to obtain the described iron/dextran complexes.

U.S. Pat. No. 4,180,567 describes a process for the production of dextran/iron complexes in which the dextran or another polyhydroxy compound is pretreated with a base at a temperature of from 85° to 100° C. The polyhydroxy compound "activated" in this way is then mixed with an aqueous solution of an iron compound which essentially contains dialysed iron(III)hydroxide. The disadvantage of this process is that first the activated dextran solution and at the same time the solution containing the dialysed iron(III)hydroxide have to be produced in two separate operations carried out in two separate apparatus. This process only gives iron/dextran complexes containing from 50 to 150 mg of Fe/ml, i.e. having an iron content of from 5 to 15 percent W/V.

The object of the present invention is to provide a simple and safe process for producing iron(III)hydroxide/dextran complexes which give stable sterile solutions for injection purposes having a high iron content of more than 20% W/V.

Accordingly, the present invention relates to a process for the production of iron(III)hydroxide/dextran complexes, in which an alkali carbonate, ammonium carbonate or a carbonate of an organic base that is inert to the reaction components and then an alkali metal hydroxide or ammonium hydroxide are added to an acid solution containing a partially depolymerised dextran and an iron(III)salt, the suspension formed is converted into solution by heating and the solution is worked up in known manner, characterised in that (a) the dextran used is a dextran having an average molecular weight of from 1000 to 10,000,
(b) from 50 to 100 kg of iron ions are used for 100 kg of dextran,
(c) from 2.0 to 2.6 vals of carbonate are slowly added to the solution of dextran and iron(III)salt,
(d) an alkali metal hydroxide or ammonium hydroxide is then added to the solution in such a quantity that, including the carbonate added, approximately 3 vals of anions are added until a pH-value of no less than about 10.5 is reached.

The process according to the invention may be carried out surprisingly easily in one apparatus, i.e. in the form of a so-called one-pot process, the solutions of the reaction components merely having to be prepared in a separate vessel.

According to the invention, preferred dextrans are dextrans having an average molecular weight of at least about 3000 and preferably of at least about 4000. The upper limit to the molecular weight is best at about 7000 and preferably at about 6000. Particularly good results have been obtained with dextrans having an average molecular weight of from about 4000 to 6000. In the context of the invention, the average molecular weight of the dextran fraction used is understood to be the weight average.

It is preferred to use a dextran solution containing at least 20 kg and preferably at least 30 kg of dextran in solution in 100 l of water. The upper limit to the concentration is best at 80 kg and preferably at 60 kg of dextran dissolved in 100 l of water.

The iron solutions used are best iron solutions containing at least about 3% and preferably at least 5% of iron(III)ions (W/W). The upper limit to the concentration of iron(III)ions is best at about 10% and preferably at about 8% (W/W).

It is best to use about 50 to 100 kg of iron(III)ions per 100 kg of dextran.

The iron(III)salts used are the salts normally used in the prior art, such as iron(III)chloride, nitrate, acetate, sulfate and other chemical equivalents. Iron(III)chloride is particularly preferred.

The solution of the dextran in water is best produced by heating, for example to between 60° and 80° C. In one preferred embodiment of the invention, the cooled solution of the dextran is allowed to run into the solution of the iron(III)salt. Accordingly, there is no need for heating and both solutions have a temperature of best less than 40° C. and preferably of the order of room temperature.

An alkali carbonate, ammonium carbonate or a carbonate of an organic base that is inert to the reaction components is then slowly added to the solution of dextran and iron(III)salt in a quantity of from 2.0 to 2.6 vals, based on the iron(III)ions. Accordingly, where iron(III)chloride is used as the iron(III)salt, from about 2.0 to 2.6 chlorine ions are replaced by hydroxyl ions after the addition. The addition of the carbonate, best in the form of an aqueous solution, is again best made at a temperature below 40° C., preferably in the absence of heating, i.e. at room temperature. The solution is preferably added very slowly over a period of more than 2 hours and, with particular preference, over a period of more than 3 hours. The carbonate solution should not be too dilute in order to avoid large quantities of liquid. Where sodium carbonate is used, which is preferred inter alia for reasons of cost, solutions having a concentration of from about 15 to 20% (W/W) and, more particularly, of from about 17 to 18%, have proved to be suitable. After the addition, the solution has a pH-value of the order of 1.5 to 2.0 and preferably of the order of 1.7 to 1.8.

An alkali metal hydroxide or ammonium hydroxide is then added. This addition is again best made in the absence of heating, i.e. under the same conditions under which the carbonate is added. It is preferred to use sodium hydroxide, again inter alia for reasons of cost, concentrations of from about 20 to 40% and preferably from about 25 to 35% (W/W) being suitable. The quantity in which the base is used is so large that substantially all the anions of the iron(III)salt are replaced by hydroxyl ions. To achieve this, it is best to use a slight excess of base which whould amount to no more than 5% and preferably to no more than 2%, based on the number of positive charges of the iron(III)ions present. The base is best added over a relatively short period, preferably over a period of from 15 to 45 minutes and more preferably over a period of from about 25 to 35 minutes.

After the base has been added, the solution has a pH value of at least about 10.5, but best of no more than 12. The pH value of the solution is preferably of the order of 11.0 to 11.5 or better still of the order of 11.2 to 11.4.

Completion of formation of the suspension may be verified by centrifuging a sample of the reaction solution. If there is no further precipitation after the addition of more alkali metal hydroxide to the clear supernatant solution, formation of the suspension may be regarded as complete.

The reaction mixture is then heated until the suspended fractions are dissolved. To this end, the reaction mixture is best heated as quickly as possible to high temperatures of at least about 80° C. to boiling point and, better still, directly to boiling point. The solution is kept at that temperature for about 40 minutes to 2 hours and preferably for about 50 to 80 minutes.

Working up of the resulting solution of the iron(III)-hydroxide/dextran complex may be carried out in known manner. Before purification and isolation, the solution may be neutralised by the addition of a solid, liquid or gaseous acid, such as a cation exchanger in the H-form, sulfuric acid or hydrochloric acid. In order to eliminate undesirably high concentrations of electrolyte in the solution, an anion exchanger in the HO-form may be additionally added to the cation or alternatively the solution may be dialysed against water. Solid preparations readily soluble in water may be obtained from the solution of the new iron complexes by known methods such as, for example, concentrating the neutral solutions by evaporation under reduced pressure or by fractional precipitation with a water-miscible organic solvent, such as for example methanol, ethanol or acetone.

In one preferred embodiment, the solution, having been cooled to a temperature below about 30° C. to room temperature, is adjusted with dilute hydrochloric acid to a slightly acid pH value, for example to a pH of from about 5 to 6 and best to a pH of the order of 5.5. After passing through a clarifying separator (for example a plate centrifuge) for the purpose of separating off relatively coarse impurities and filtration of the solution, the complex may be precipitated by the addition of a suitable water-miscible solvent. As in the prior art, ethanol is preferably used for this purpose. The deposit is separated off, dried and contains about 28 to 35% by weight of Fe.

It is surprisingly possible to be able to dissolve the complex obtained by the process according to the invention in a high concentration in water, for example in a concentration of from 15 to 25% of Fe and preferably in a concetration of the order of 20% of Fe or higher (W/V).

The present invention also relates to sterile aqueous pharmaceutical solutions for the treatment of iron deficiencies containing the iron(III)hydroxide/dextran complex obtainable by the process described in the foregoing and the usual additives. To produce a solution such as this, the complex is dissolved in water by heating, for example to temperatures of from about 60° to 80° C. The solution is then sterilised. Standard additives for the sterilised aqueous solution include for example phenol in a quantity of 0.5%.

EXAMPLE 80 kg of dextran (molecular weight 5000) are dissolved in 180 liters of water at 70° C. The solution cooled to room temperature is allowed to run into 877 kg of an aqueous $FeCl_3$ solution (6.4 W/W % of Fe, density at 20° C.=1.170). 751 kg of an aqueous soda solution (17.2% W/W of $Na_2CO_3$, density at 20° C.=1.185) are added to this mixed solution over a period of 3.5 hours with stirring (mechanical stirrer) at 25° C. In this way, approximately 2.3 $Cl^-$ are replaced by $OH^-$ in the $FeCl_3$ (corresponding to $Fe(OH)_{2.3}Cl_{0.7}$). At the same time, the pH of the reaction solution reaches a value of approximately 1.7. A pH-value of approximately 11 is obtained after the addition of 93 kg of sodium hydroxide (30 W/W % of NaOH, density at 20° C.=1.330) over a period of about 30 minutes. The suspension thus formed is heated to boiling temperature and kept at that temperature for about 1 hour. The resulting iron(III)hydroxide/dextran complex solution is cooled to 25° C. and adjusted to pH 5.5 with 21 kg of dilute hydrochloric acid (20.4 W/W % of HCl, density at 20° C.=1.100). After passing through a clarifying separator (plate centrifuge) for the purpose of separating off relatively coarse impurities and filtration of the solution through a multilayer filter, the product is precipitated with ethanol. The deposit is washed with ethanol in a mixer, separated off and dried in vacuo. The dry material has an iron content of from 28 to 35% W/W. The dry iron complex is processed in distilled, pyrogen-free water at 70° C. to form a sterile injection solution containing 20 W/V % of iron and 0.5% W/W of phenol as preservative. The solution has a relative viscosity of less than 40, as measured at 25° C.

We claim:

1. A process for producing stable, sterile aqueous pharmaceutical solution for the treatment of iron deficiencies containing the iron(III)hydroxide/dextran complex comprising:
 (a) dissolving dextran having an average molecular weight of from 3,000 to 6,000 in water;
 (b) cooling the dextran solution to a temperature of less than 40° C.;
 (c) adding the cooled dextran solution to a solution of $FeCl_3$ at a temperature of less than 40° C. to form a mixed solution having a weight ratio of from 50 to 100 kg of iron ions per 100 kg of dextran;
 (d) adding from 2.0 to 2.6 vals of carbonate selected from the group consisting of alkali metal carbonates, ammonium carbonate and carbonates of organic bases inert to the reaction components to said mixed solution over a period of more than two hours;
 (e) adding an alkali metal hydroxide or ammonium hydroxide to the solution of step (d) to yield a suspension having a pH of at least about 10.5;
 (f) recovering the iron(III)/dextran complex;
 (g) dissolving said iron(III)/dextran complex in water to yield a stable solution having an iron content of at least 15% W/V.

2. The process of claim 1, wherein about 3 vals of anions, including the carbonate, are added to yield said pH in step (e).

3. The process of claim 1, wherein said dextran has a molecular weight of from about 4000 to 6000.

4. The process of claim 1, wherein said cooled dextran solution is slowly run into said $FeCl_3$ solution.

5. The process of claim 4, wherein said dextran is cooled to room temperature in step (b).

6. The process of claim 1, wherein said carbonate is added to said mixed solution at a temperature of less than 40° C.

7. The process of claim 6, wherein said carbonate is added to said mixed solution at room temperature.

8. The process of claim 1, wherein said carbonate is added to said mixed solution slowly over a period of more than three hours.

9. The process of claim 1, wherein said addition of alkali metal hydroxide or ammonium hydroxide is added over a period of from 15 to 45 minutes.

10. The process of claim 1, wherein said stable, sterile aqueous pharmaceutical solution contains iron in a concentration of from 15% to 25% W/V.

11. The process of claim 10, wherein said iron concentration is at least 20% W/V.

* * * * *